(12) United States Patent
Wu

(10) Patent No.: US 6,248,719 B1
(45) Date of Patent: Jun. 19, 2001

(54) TRICYCLIC 3-KETO DERIVATIVES OF 6-O-METHYLERTHROMYCIN

(75) Inventor: Yong-Jin Wu, East Lyme, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/485,965
(22) PCT Filed: May 12, 1999
(86) PCT No.: PCT/IB99/00855
§ 371 Date: Feb. 18, 2000
§ 102(e) Date: Feb. 18, 2000
(87) PCT Pub. No.: WO99/62920
PCT Pub. Date: Dec. 9, 1999

Related U.S. Application Data

(60) Provisional application No. 60/087,798, filed on Jun. 3, 1998.

(51) Int. Cl.⁷ ............................. A61K 31/70; C07H 17/08
(52) U.S. Cl. .............................................. 514/29; 536/7.4
(58) Field of Search .................................. 536/7.4; 514/29

(56) References Cited

FOREIGN PATENT DOCUMENTS

| | | |
|---|---|---|
| 0638585 | 4/1993 | (EP) . |
| 2732023 | 3/1995 | (FR) . |
| 9717356 | 5/1997 | (WO) . |
| 9921865 | 5/1999 | (WO) . |
| 9921866 | 5/1999 | (WO) . |

*Primary Examiner*—Elli Peselev
(74) *Attorney, Agent, or Firm*—Peter C. Richardson; Paul H. Ginsburg; Jeffrey N. Myers

(57) ABSTRACT

The present invention relates to compounds of the formula 1

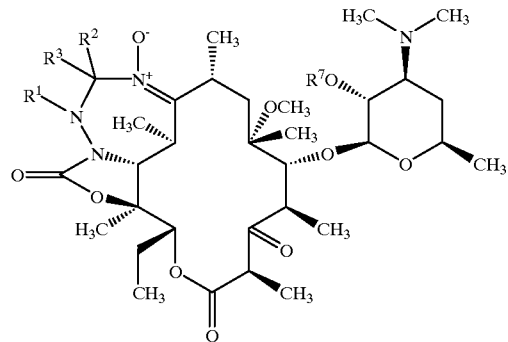

and to pharmaceutically acceptable salts thereof, wherein $R^1$–$R^7$ are as defined herein. The compounds of formula 1 are useful as antibiotic agents. The invention further relates to pharmaceutical compositions and methods of treating bacterial infection using such compounds, and to methods of making the compounds of formula 1.

17 Claims, No Drawings

TRICYCLIC 3-KETO DERIVATIVES OF 6-O-METHYLERTHROMYCIN

CROSS REFERENCE TO RELATED APPLICATIONS

This application is the National Stage of International Application No. PCT/IB99/00855, filed May 12, 1999, which claims the benefit of U.S. provisional application no. 60/087,798, filed Jun. 3, 1998.

BACKGROUND OF THE INVENTION

This invention relates to tricyclic 3-keto derivatives of 6-O-methylerythromycin A. The compounds of this invention are useful as antibiotic agents in mammals, including man, as well as in fish and birds. The compounds of the present invention are broad-spectrum macrolide antibiotics that are effective against infections caused by certain gram-positive and gram-negative bacteria as well as protozoa.

Macrolide antibiotics are known to be useful in the treatment of a broad spectrum of bacterial infections and protozoa infections in mammals, fish and birds. Such antibiotics include various derivatives of erythromycin A such as azithromycin which is commercially available and is referred to in U.S. Pat. Nos. 4,474,768 and 4,517,359, both of which are incorporated herein by reference in their entirety. Additional macrolides are referred to in U.S. patent application Ser. No. 60/063676, filed Oct. 29, 1997 (Yong-Jin Wu), U.S. application Ser. No. 60/063161, filed Oct. 29, 1997 (Yong-Jin Wu), U.S. application Ser. No. 60/054866, filed Aug. 6, 1997(Hiroko Masamune, Yong-Jin Wu, Takushi Kaneko and Paul R. McGuirk), all of which are incorporated herein by reference in their entirety. Like azithromycin and other macrolide antibiotics, the novel macrolide compounds of the present invention possess activity against various bacterial infections and protozoa infections as described below.

SUMMARY OF THE INVENTION

The present invention relates to compounds of the formula

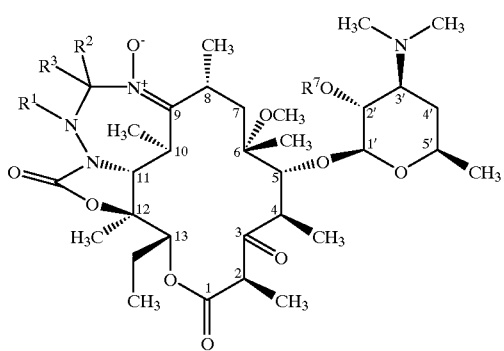

1 and to pharmaceutically acceptable salts thereof, wherein:

$R^1$ is selected from H, $-(CR^4R^5)_m R^6$, $-C(O)(CR^4R^5)_m R^6$, $-C(O)O(CR^4R^5)_m R^6$, $-C(O)NR^4(CR^4R^5)_m R^6$, wherein m is an integer ranging from 0 to 6 and both $R^4$ and $R^5$ may vary for each iteration where m is greater than 1;

each $R^2$ and $R^3$ are independently selected from H and $C_1$-$C_{18}$ alkyl, wherein one or two carbons of said alkyl are optionally replaced by a heteroatom selected from O, S and N, and are optionally substituted by 1 to 3 substituents independently selected from the group consisting of $-C(O)$ $O(C_1$-$C_{10})$alkyl, $-O(C_1$-$C_{10})$alkyl, $C_1$-$C_{10}$ alkanoyl, halo, nitro, cyano, $C_1$-$C_{10}$ alkyl, 4–10 membered heterocyclic, $C_6$-$C_{10}$ aryl, $-NH(C_1$-$C_{10})$alkyl, $-S(C_1$-$C_{10}$ alkyl), $-SO$ $(C_1$-$C_{10})$alkyl, $-SO_2(C_1$-$C_{10})$alkyl and $-SO_2N(C_1$-$C_{10})$ alkyl, provided that two O atoms, two S atoms or an S and an O atom are not bonded to each other;

each $R^4$ and $R^5$ are independently selected from H, halo and $C_1$-$C_6$ alkyl, wherein 1 to 3 carbons of said alkyl are optionally replaced by a heteroatom selected from O, S and N and each $R^4$ and $R^5$ may vary independently when m is greater than 1, provided that two O atoms, two S atoms or an S and an O atom are not bonded to each other; or each $R^4$ and $R^5$ taken together with the carbon to which they are attached can form a 3–10 membered ring, wherein one or more carbons of said ring are optionally replaced by a heteroatom selected from O, S and N, and are optionally substituted by 1 to 3 substituents independently selected from the group consisting of $-C(O)O(C_1$-$C_{10})$alkyl, $-O(C_1$-$C_{10})$alkyl, $C_1$-$C_{10}$ alkanoyl, halo, nitro, cyano, $C_1$-$C_{10}$ alkyl, 4–10 membered heterocyclic, $C_6$-$C_{10}$ aryl, $-NH(C_1$-$C_{10})$alkyl, $-N((C_1$-$C_{10})$alkyl)$_2$, $-S(C_1$-$C_{10})$ alkyl, $-SO(C_1$-$C_{10})$alkyl, $-SO_2(C_2(C_1$-$C_{10})$alkyl and $-SO_2N(C_1$-$C_{10})$alkyl, provided that two O atoms, two S atoms or an S and an O atom are not bonded to each other;

$R^6$ is $(C_1$-$C_{18})$alkyl, a 4–10 membered heterocyclic or $C_6$-$C_{10}$ aryl, wherein 1 to 3 carbons of said alkyl are optionally replaced by a heteroatom selected from O, S and N and said heterocycic and aryl groups are optionally substituted by 1 to 3 substituents independently selected from the group consisting of $-C(O)O(C_1$-$C_{10})$alkyl, $-O(C_1$-$C_{10})$alkyl, $C_1$-$C_{10}$ alkanoyl, halo, nitro, cyano, $(C_1$-$C_{10})$ alkyl, $-NH(C_1$-$C_{10})$alkyl, $-N((C_1$-$C_{10})$alkyl)$_2$, $-S(C_1$-$C_{10}$ alkyl), $-SO(C_1$-$C_{10})$alkyl, $-SO_2(C_1$-$C_{10})$ alkyl and $-SO_2N(C_1$-$C_{10})$alkyl, provided that two O atoms, two S atoms or an S and an O atom are not bonded to each other; and $R^7$ is H, $-C(O)O(C_1$-$C_{18})$alkyl or $-C(O)(C_1$-$C_{18})$alkyl, wherein 1 to 3 carbons of said alkyl are optionally replaced by a heteroatom selected from O, S and N and wherein in the alkyl portion of said alkanoyl one or two carbons optionally may be replaced by a heteroatom selected from O, S and N, provided that two O atoms, two S atoms or an S and an O atom are not bonded to each other.

More specific embodiments of this invention include compounds of formula 1 wherein $R^7$ is H.

More specific embodiments of this invention include compounds of formula 1 wherein $R^3$ is H.

More specific embodiments of this invention include compounds of formula 1 wherein $R^3=R^2=H$.

More specific embodiments of this invention include compounds of formula 1 wherein $R^3=R^2=R^7=H$.

Other more specific embodiments of this invention include compounds of formula 1 wherein $R^2$ is $(CH_2)_m R^6$, wherein m is an integer ranging from 0 to 6. Specific embodiments of compounds of formula 1 wherein $R^2$ is $(CH_2)_m R^6$ and wherein m is an integer ranging from 0 to 6 include such compounds wherein $R^6$ is quinolin-4-yl, quinolin-5-yl, quinolin-8-yl, 4-phenyl-1-imidazol-1-yl, 4-pyridin-3-yl-imidazol-1-yl, or imidazo(4,5-b)pyridin-3-yl. More specific embodiments of this invention include compounds of formula 1 wherein $R^2$ is $(CH_2)_m R^6$ and m is 3. Specific embodiments of compounds of formula 1 wherein $R^2$ is $(CH_2)_m R^6$ and m is 3 include such compounds wherein $R^6$ is quinolin-4-yl, quinolin-5-yl, quinolin-8-yl, 4-phenyl-1-imidazol-1-yl, 4-pyridin-3-yl-imidazol-1-yl or imidazo(4,5-b)pyridin-3-yl.

Examples of preferred compounds of this invention include:

the compound of formula 1 wherein $R^7$=H, $R^3$=$R^2$=H, $R^1$=3-quinolin-4-yl-propyl;

the compound of formula 1 wherein $R^7$=H, $R^3$=$R^2$=H, $R^1$=7-methoxy-quinolin-4-yl)-propyl;

the compound of formula 1 wherein $R^7$=H, $R^3$=$R^2$=H, $R^1$=3-benzoimidazol-1-yl-propyl;

the compound of formula 1 wherein $R^7$=H, $R^3$=$R^2$=H, $R^1$=3-indol-1-yl-propyl;

the compound of formula 1 wherein $R^7$=H, $R^3$=$R^2$=H, $R^1$=3-indazol-1-yl-propyl;

the compound of formula 1 wherein $R^7$=H, $R^3$=$R^2$=H, $R^1$=3-carbazol-1-yl-propyl;

the compound of formula 1 wherein $R^7$=H, $R^3$=$R^2$=H, $R^1$=3-(5-phenyl-1H-pyrrol-2-yl)-propyl;

the compound of formula 1 wherein $R^7$=H, $R^3$=$R^2$=H, $R^1$=3-(4-phenyl-imidazol-1-yl)-propyl;

the compound of formula 1 wherein $R^7$=H, $R^3$=$R^2$=H, $R^1$=3-(imidazo(4,5-b)pyridin-3-yl)-propyl;

the compound of formula 1 wherein $R^7$=H, $R^3$=$R^2$=H, $R^1$=3-(4-pyridin-3-yl-imidazol-1-yl)-propyl;

the compound of formula 1 wherein $R^7$=H, $R^3$=$R^2$=H, $R^1$=3-(3-(4-chlorophenyl)-(1,2,4)oxadizol-5-yl)-propyl;

the compound of formula 1 wherein $R^7$=H, $R^3$=$R^2$=H, $R^1$=3-(3-(4-methoxyphenyl)-(1,2,4)oxadizol-5-yl)-propyl;

the compound of formula 1 wherein $R^7$=H, $R^3$=$R^2$=H, $R^1$=3-(3-(4-pyridin-4-yl)-(1,2,4)oxadizol-5-yl)-propyl;

the compound of formula 1 wherein $R^7$=H, $R^3$=$R^2$=H, $R^1$=3-benzotriazol-1-yl-propyl;

the compound of formula 1 wherein $R^7$=H, $R^3$=$R^2$=H, $R^1$=3-benzotriazol-2-yl-propyl;

the compound of formula 1 wherein $R^7$=H, $R^3$=$R^2$=H, $R^1$=3-(1H-indol-3-yl)-propyl;

the compound of formula 1 wherein $R^7$=H, $R^3$=$R^2$=H, $R^1$=3-pyridin-4-yl-propyl;

the compound of formula 1 wherein $R^7$=H, $R^3$=$R^2$=H, $R^1$=3-pyridin-3-yl-propyl;

the compound of formula 1 wherein $R^7$=H, $R^3$=$R^2$=H, $R^1$=3-pyridin-2-yl-propyl;

the compound of formula 1 wherein $R^7$=H, $R^3$=$R^2$=H, $R^1$=3-phenylpropyl;

the compound of formula 1 wherein $R^7$=H, $R^3$=$R^2$=H, $R^1$=3-(2-methoxyphenyl)-propyl;

the compound of formula 1 wherein $R^7$=H, $R^3$=$R^2$=H, $R^1$=3-furan-2-yl-propyl;

the compound of formula 1 wherein $R^7$=H, $R^3$=$R^2$=H, $R^1$=3-thiophen-2-yl-propyl;

the compound of formula 1 wherein $R^7$=H, $R^3$=$R^2$=H, $R^1$=3-pyrrol-1-yl-propyl;

the compound of formula 1 wherein $R^7$=H, $R^3$=$R^2$=H, $R^1$=3-(2-pyridin-3-yl-thiazol-4-yl)-propyl;

the compound of formula 1 wherein $R^7$=H, $R^3$=$R^2$=H, $R^1$=3-(2-phenyl-thiazol-5-yl)-propyl;

the compound of formula 1 wherein $R^7$=H, $R^3$=$R^2$=H, $R^1$=3-(2-phenyl-thiazol-5-yl)-propyl;

the compound of formula 1 wherein $R^7$=H, $R^3$=$R^2$=H, $R^1$=3-(4-phenyl1H-imidazol-2-yl)-propyl;

and pharmaceutically acceptable salts of the foregoing compounds.

The invention also relates to a pharmaceutical composition for the treatment of a bacterial infection or protozoal infection in a mammal, fish, or bird which comprises a therapeutically effective amount of a compound of formula 1, or a pharmaceutically acceptable salt thereof, and a pharmaceutically acceptable carrier.

The invention also relates to a method of treating a bacterial infection or a protozoal infection in a mammal, fish, or bird which comprises administering to said mammal, fish or bird a therapeutically effective amount of a compound of formula 1 or a pharmaceutically acceptable salt thereof.

The term "treatment", as used herein, unless otherwise indicated, includes the treatment or prevention of a bacterial infection or protozoal infection as provided in the method of the present invention.

As used herein, unless otherwise indicated, the term "bacterial infection(s)" or "protozoa infection" includes bacterial infections and protozoa infections that occur in mammals, fish and birds as well as disorders related to bacterial infections and protozoa infections that may be treated or prevented by administering antibiotics such as the compounds of the present invention. Such bacterial infections and protozoa infections and disorders related to such infections include the following: pneumonia, otitis media, sinusitus, bronchitis, tonsillitis, and mastoiditis related to infection by *Streptococcus pneumoniae, Haemophilus influenzae, Moraxella catarrhalis, Staphylococcus aureus,* or *Peptostreptococcus* spp.; pharynigitis, rheumatic fever, and glomerulonephritis related to infection by *Streptococcus pyogenes,* Groups C and G streptococci, *Clostridium diptheriae,* or *Actinobacillus haemolyticum*; respiratory tract infections related to infection by *Mycoplasma pneumoniae, Legionella pneumophila, Streptococcus pneumoniae, Haemophilus influenzae,* or *Chlamydia pneumoniae*; uncomplicated skin and soft tissue infections, abscesses and osteomyelitis, and puerperal fever related to infection by *Staphylococcus aureus,* coagulase-positive staphylococci (i.e., *S. epidermidis, S. hemolyticus,* etc.), *Streptococcus pyogenes, Streptococcus agalactiae,* Streptococcal groups C-F (minute-colony streptococci), viridans streptococci, *Corynebacterium minutissimum, Clostridium* spp., or *Bartonella henselae*; uncomplicated acute urinary tract infections related to infection by *Staphylococcus saprophyticus* or *Enterococcus* spp.; urethritis and cervicitis; and sexually transmitted diseases related to infection by *Chlamydia trachomatis, Haemophilus ducreyl, Treponema pallidum, Ureaplasma urealyticum,* or *Neiserria gonorrheae*; toxin diseases related to infection by *S. aureus* (food poisoning and Toxic shock syndrome), or Groups A, B, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H. influenzae,* or *Listeria* spp.; disseminated *Mycobacterium avium* complex (MAC) disease related to infection by *Mycobacterium avium,* or *Mycobacterium intracellulare*; gastroenteritis related to infection by *Campylobacter jejuni*; intestinal protozoa related to infection by *Cryptosporidium* spp.; odontogenic infection related to infection by viridans streptococci; persistent cough related to infection by *Bordetella pertussis*; gas gangrene related to infection by *Clostridium perfringens* or *Bacteroides* spp.; and atherosclerosis related to infection by *Helicobacter pylori* or *Chlamydia pneumoniae*. Bacterial infections and protozoa infections and disorders related to such infections that may be treated or prevented in animals include the following: bovine respiratory disease related to infection by *P. haem., P multocida, Mycoplasma bovis,* or *Bordetella* spp.; cow enteric disease related to infection by *E. Coli* or protozoa (i.e., coccidia, cryptosporidia, etc.); dairy cow mastitis related to infection by *Staph. aureus, Strep. uberis, Strep. agalactiae, Strep. dysgalactiae, Klebsiella* spp., *Corynebacterium,* or *Enterococcus* spp.; swine respiratory disease related to infection by A. pleuro., P. multocida, or Mycoplasma spp.; swine enteric disease related to infection by E. coli, Lawsonia intracellularis, Salmonella, or Serpulina hyodyisinteriae; cow footrot related to infection by Fusobacterium spp.; cow metritis related to infection by E coli; cow hairy warts related to infection by Fusobacterium necrophorum or Bacteroides nodosus; cow pink-eye related to infection by Moraxella bovis; cow premature abortion related to infection by protozoa (i.e. neosporium); urinary tract infection in dogs and cats related to infection by E coli; skin and soft tissue infections in dogs and cats related to infection by Staph. epidermidis, Staph. intermedius, coagulase neg. Staph. or P. multocida; and dental or mouth infections in dogs and cats related to infection by Alcaligenes spp., Bacteroides spp., Clostridium spp., Enterobacter spp., Eubacterium, Peptostreptococcus, Porphyromonas, or Prevotella. Other bacterial infections and protozoa infections and disorders related to such infections that may be treated or prevented in accord with the method of the present invention are referred to in J. P. Sanford et al., "The Sanford Guide To Antimicrobial Therapy," 26th Edition, (Antimicrobial Therapy, Inc., 1996).

The invention also relates to a method of preparing a compound of the formula

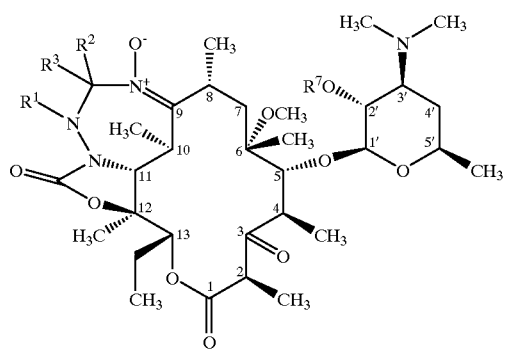

and to pharmaceutically acceptable salts thereof, wherein:
$R^1$ is selected from H, —$(CR^4R^5)_m R^6$, —$C(O)(CR^4R^5)_m R^6$, —$C(O)O(CR^4R^5)_m R^6$, —$C(O)NR^4(CR^4R^5)_m R^6$, wherein m is an integer ranging from 0 to 6 and both $R^4$ and $R^5$ may vary for each iteration where m is greater than 1;

each $R^2$ and $R^3$ are independently selected from H and $C_1$–$C_{18}$ alkyl, wherein one or two carbons of said alkyl are optionally replaced by a heteroatom selected from O, S and N, and are optionally substituted by 1 to 3 substituents independently selected from the group consisting of —C(O)O($C_1$–$C_{10}$)alkyl, —O($C_1$–$C_{10}$)alkyl, $C_1$–$C_{10}$ alkanoyl, halo, nitro, cyano, $C_1$–$C_{10}$ alkyl, 4–10 membered heterocyclic, $C_6$–$C_{10}$ aryl, —NH($C_1$–$C_{10}$)alkyl, —S($C_1$–$C_{10}$ alkyl), —SO($C_1$–$C_{10}$)alkyl, —$SO_2$($C_1$–$C_{10}$)alkyl and —$SO_2$N($C_1$14 $C_{10}$)alkyl, provided that two O atoms, two S atoms or an S and an O atom are not bonded to each other;

each $R^4$ and $R^5$ are independently selected from H, halo and $C_1$–$C_6$ alkyl, wherein 1 to 3 carbons of said alkyl are optionally replaced by a heteroatom selected from O, S and N and each $R^4$ and $R^5$ may vary independently when m is greater than 1, provided that two O atoms, two S atoms or an S and an O atom are not bonded to each other; or each $R^4$ and $R^5$ taken together with the carbon to which they are attached can form a 3–10 membered ring, wherein one or more carbons of said ring are optionally replaced by a heteroatom selected from O, S and N, and are optionally substituted by 1 to 3 substituents independently-selected from the group consisting of —C(O)O($C_1$–$C_{10}$)alkyl, —O($C_1$–$C_{10}$)alkyl, $C_1$–$C_{10}$ alkanoyl, halo, nitro, cyano, $C_1$–$C_{10}$ alkyl, 4–10 membered heterocyclic, $C_6$–$C_{10}$ , aryl, —NH($C_1$–$C_{10}$)alkyl, —N(($C_1$–$C_{10}$)alkyl)$_2$, —S($C_1$–$C_{10}$) alkyl, —SO($C_1$–$C_{10}$)alkyl, —$SO_2$($C_2$($C_1$–$C_{10}$)alkyl and —$SO_2$N($C_1$–$C_{10}$)alkyl, provided that two O atoms, two S atoms or an S and an O atom are not bonded to each other;

$R^6$ is ($C_1$–$C_{18}$)alkyl, a 4–10 membered heterocyclic or $C_6$–$C_{10}$ aryl, wherein 1 to 3 carbons of said alkyl are optionally replaced by a heteroatom selected from O, S and N and said heterocycic and aryl groups are optionally substituted by 1 to 3 substituents independently selected from the group consisting of —C(O)O($C_1$–$C_{10}$)alkyl, —O($C_1$–$C_{10}$)alkyl, $C_1$–$C_{10}$ alkanoyl, halo, nitro, cyano, ($C_1$–$C_{10}$) alkyl, —NH($C_1$–$C_{10}$)alkyl, —N(($C_1$–$C_{10}$)alkyl)$_2$, —S($C_1$–$C_{10}$ alkyl), —SO($C_1$–$C_{10}$ )alkyl, —$SO_2$($C_1$–$C_{10}$) alkyl and —$SO_2$N($C_1$–$C_{10}$)alkyl, provided that two O atoms, two S atoms or an S and an O atom are not bonded to each other; and $R^7$ is H, —C(O)O($C_1$–$c_{18}$)alkyl or —C(O)($C_1$–$c_{18}$)alkyl, wherein 1to 3 carbons of said alkyl are optionally replaced by a heteroatom selected from O, S and N and wherein in the alkyl portion of said alkanoyl one or two carbons optionally may be replaced by a heteroatom selected from O, S and N, provided that two O atoms, two S atoms or an S and an O atom are not bonded to each other, which comprises treating a compound of the formula

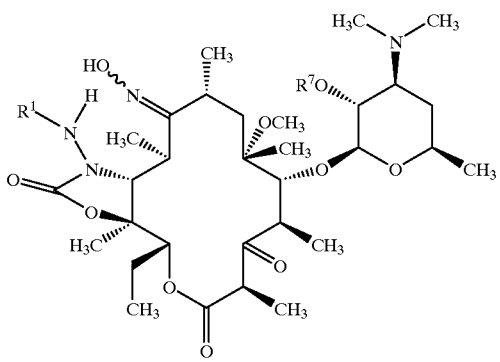

wherein $R^7$ and $R^1$ are as defined above, with a compound of the formula $R^3R^2C=O$, wherein $R^3$ and $R^2$ are as defined for the compound of formula 1, in the presence of an acid. An example of a preferred compound of the formula $R^3R^2C=O$ is $CH_2O$. Examples of suitable acids include, for example, acetic acid, formic acid, para-toluene sulfonic acid and proprionic acid. The acid may be in the presence of a suitable solvent, such as for example, $CH_2Cl_2$, $C_6H_6$, $CHCl_3$, acetonitrile, dimethylformamide, tetrahydrofuran, dioxane and dichloroethane.

The compound of formula 2 can be prepared as described in U.S. patent application Ser. No. 60/049349, filed Jun. 11, 1997 (Yong-Jin Wu), and in corresponding International Application no. WO 9856800, published Dec. 17, 1998, which is herein incorporated by reference in its entirety.

The present invention further relates to a compound of the formula

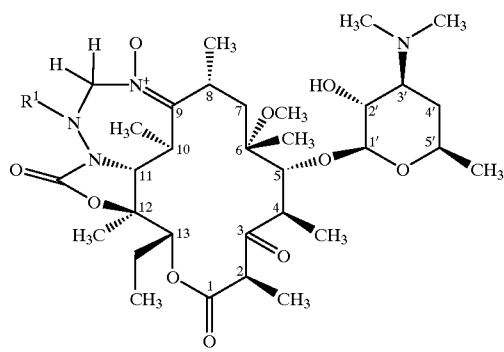

and to pharmaceutically acceptable salts thereof, wherein:

$R^1$ is selected from H, $-(CR^4R^5)_m R^6$, $-C(O)(CR^4R^5)_m R^6$, $-C(O)O(CR^4R^5)_m R^6$, $-C(O)NR^4(CR^4R^5)_m R^6$, wherein m is an integer ranging from 0 to 6 and both $R^4$ and $R^5$ may vary for each iteration where m is greater than 1;

each $R^4$ and $R^5$ are independently selected from H, halo and $C_1$–$C_6$ alkyl, wherein 1 to 3 carbons of said alkyl are optionally replaced by a heteroatom selected from O, S and N and each $R^4$ and $R^5$ may vary independently when m is greater than 1, provided that two O atoms, two S atoms or an S and an O atom are not bonded to each other; or each $R^4$ and $R^5$ taken together with the carbon to which they are attached can form a 3–10 membered ring, wherein one or more carbons of said ring are optionally replaced by a heteroatom selected from O, S and N, and are optionally substituted by 1 to 3 substituents independently selected from the group consisting of $-C(O)O(C_1$–$C_{10})$alkyl, $-O(C_1$–$C_{10})$alkyl, $C_1$–$C_{10}$ alkanoyl, halo, nitro, cyano, $C_1$–$C_{10}$ alkyl, 4–10 membered heterocyclic, $C_6$–$C_{10}$ aryl, $-NH(C_1$–$C_{10})$alkyl, $-N((C_1$–$C_{10})$alkyl$)_2$, $-S(C_1$–$C_{10})$alkyl, $-SO(C_1$–$C_{10})$alkyl, $-SO_2(C_2(C_1$–$C_{10})$alkyl and $-SO_2N(C_1$–$C_{10})$alkyl, provided that two O atoms, two S atoms or an S and an O atom are not bonded to each other; and $R^6$ is $(C_1$–$C_{18})$alkyl, a 4–10 membered heterocyclic or $C_6$–$C_{10}$ aryl, wherein 1 to 3 carbons of said alkyl are optionally replaced by a heteroatom selected from O, S and N and said heterocyic and aryl groups are optionally substituted by 1 to 3 substituents independently selected from the group consisting of $-C(O)O(C_1$–$C_{10})$alkyl, $-O(C_1$–$C_{10})$alkyl, $C_1$–$C_{10}$ alkanoyl, halo, nitro, cyano, $(C_1$–$C_{10})$ alkyl, $-NH(C_1$–$C_{10})$alkyl, $-N((C_1$–$C_{10})$alkyl$)_2$, $-S(C_1$–$C_{10}$ alkyl), $-SO(C_1$–$C_{10})$alkyl, $-SO_2(C_1$–$C_{10})$alkyl and $-SO_2N(C_1$–$C_{10})$alkyl, provided that two O atoms, two S atoms or an S and an O atom are not bonded to each other.

The present invention further relates to a compound of the formula

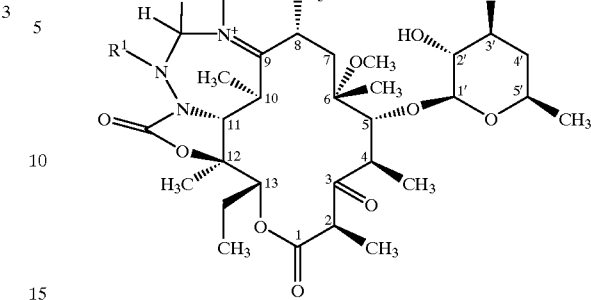

and pharmaceutically acceptable salts thereof, wherein:

$R^1$ is selected from the group consisting of: phenylbutyl, 3-quinolin-4-yl-propyl, 3-(4-phenyl-imadazol-1-yl)-propyl, 3-(2-methoxyphenyl)-propyl, 3-furan-2-yl-propyl, 3-benzoimidazol-1-yl-propyl, 3-indazol-1-yl-propyl, 3-(4-hydroxy-phenyl)-propyl, 3-(1H-indol-3-yl)-propyl, and 3-(4-pyridin-3-yl-imidazol-1-yl)-propyl.

In the chemical structures depicted herein, a wavy line indicates that the stereochemistry at the chiral center to which the wavy line is connected is either an R or S configuration where the wavy line is connected to a carbon atom. In the compound of formula 2, the wavy line connected to the oxime nitrogen at position 9 of the macrolide ring indicates that the hydroxy moiety is in an E or Z configuration.

The term "halo", as used herein, unless otherwise indicated, means fluoro, chloro, bromo or iodo. Preferred halo groups are fluoro, chloro and bromo.

The term "alkyl", as used herein, unless otherwise indicated, includes saturated monovalent hydrocarbon radicals having straight, cyclic or branched moieties. Said alkyl group may include one or two double or triple bonds. It is understood that for cyclic moieties at least three carbon atoms are required in said alkyl group.

The term "alkanoyl", as used herein, unless otherwise indicated, includes -C(O)-alkyl groups wherein "alkyl" is as defined above.

The term "aryl", as used herein, unless otherwise indicated, includes an organic radical derived from an aromatic hydrocarbon by removal of one hydrogen, such as phenyl or naphthyl.

The term "4–10 membered heterocyclic", as used herein, unless otherwise indicated, includes aromatic and non-aromatic heterocyclic groups containing one or more heteroatoms each selected from O, S and N, wherein each heterocyclic group has from 4–10 atoms in its ring system. Non-aromatic heterocyclic groups include groups having only 4 atoms in their ring system, but aromatic heterocyclic groups must have at least 5 atoms in their ring system. The heterocyclic groups include benzo-fused ring systems and ring systems substituted with one or more oxo moieties. An example of a 5 membered heterocyclic group is thiazolyl, and an example of a 10 membered heterocyclic group is quinolinyl. Examples of non-aromatic heterocyclic groups are pyrrolidinyl, piperidino, morpholino, thiomorpholino and piperazinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl and thiazolyl. In general, acceptable 4–10 membered heterocyclic groups include those derived from one of the following: furan, thiophene, 2H-pyrrole, pyrrole, 2-pyrroline, 3-pyrroline, pyrrolidine, 1,3-dioxolane, oxazole, thiazole, imidazole, 2-imidazole, imidazolidine, pyrazole, 2-pyrazoline, pyrazolidine, isoxazole, isothiazole, 1,2,3-oxadiazole, 1,2,3-triazole, 1,3,4-thiadiazole, 2H-pyran, 4H-pyran, pyridine, piperidine, 1,4-dioxane, 1,3-dioxane, morpholine, 1,4-dithiane, thiomorpholine, pyridazine, pyrimidine, pyrazine, piperazine, 1,3,5-triazine, 1,3,5-trithiane, indolizine, indole, isoindole, 3H-indole, indoline, benzofuran, benzothiophene, 1 H-indazole, benzimidazole, benzthiazole, purine, 4H-quinolizine, quinoline, isoquinoline, cinnoline, phthalazine, quinazoline, quinoxaline, 1,8-naphthyridine, pteridine, quinuclidine, carbazole, acridine, phenazine, phenothiazine, phenoxazine, tetrazole, thietane and azetidine.

The phrase "pharmaceutically acceptable salt(s)", as used herein, unless otherwise indicated, includes salts of acidic or basic groups which may be present in the compounds of formula 1. The compounds of formula 1 that are basic in nature are capable of forming a wide variety of salts with various inorganic and organic acids. The acids that may be used to prepare pharmaceutically acceptable acid addition salts of such basic compounds of formula 1 are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts.

Those compounds of the formula 1 that are acidic in nature, are capable of forming base salts with various pharmacologically acceptable cations. Examples of such salts include the alkali metal or alkaline earth metal salts and particularly, the sodium and potassium salts.

The present invention also includes all radiolabelled forms of the compounds of formula 1, and pharmaceutically acceptable salts thereof, wherein the radiolabel is selected from $^3H$, $^{11}C$ and $^{14}C$. Such radiolabelled compounds are useful as research or diagnostic tools.

Certain compounds of formula 1 may have asymmetric centers and therefore exist in different enantiomeric forms. This invention relates to the use of all optical isomers and stereoisomers of the compounds of formula 1 and mixtures thereof. The compounds of formula 1 may also exist as tautomers. This invention relates to the use of all such tautomers and mixtures thereof.

DETAILED DESCRIPTION OF THE INVENTION

The preparation of the compounds of the present invention is illustrated in the following Scheme.

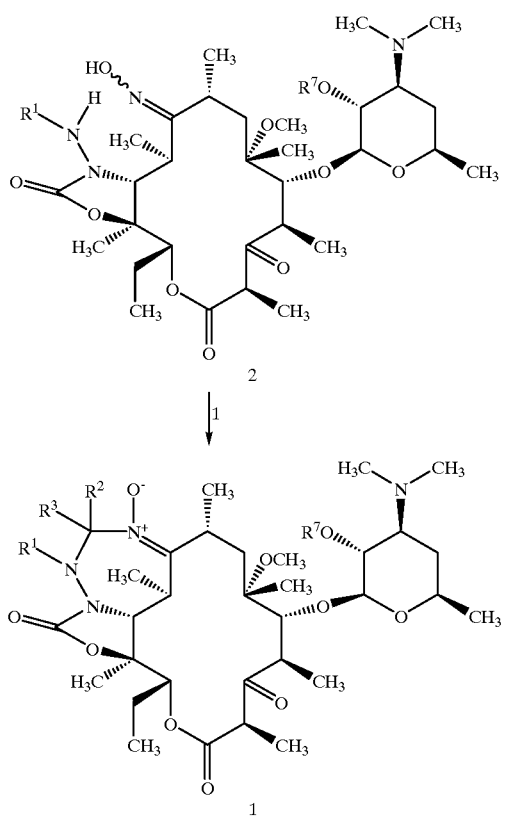

Scheme

The Scheme illustrates the general synthesis of the compounds of the present invention. In the Scheme, the starting compound of formula 2 can be prepared as described in U.S. patent application Ser. No. 60/049349, filed Jun. 11, 1997 (Yong-Jin Wu), and in corresponding International Application no. WO 9856800, published Dec. 17, 1998, which are herein incorporated by reference in its entirety.

The tricyclic nitrone of the compound of formula 1 can be prepared by treating the starting compound of formula 2 with a compound of the formula $R^3R^2C=O$, wherein $R^3$ and $R^2$ are defined as specified in the compound of formula 1, in the presence of an acid such as formic acid, acetic acid, para-toluenesulfonic acid or proprionic acid in a solvent such as $CHCl_3$, chloroform, benzene, acetonitrile, dimethylformamide (DMF), tetrahydrofuran (THF), dioxane or dichloroethane, at a temperature within the range from about 10 to about 90° C. for a period of about 1 to 18 hours.

The compounds of the present invention may have asymmetric carbon atoms. Such diasteromeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomric mixture by reaction with an appropriate optically active compound (e.g., alcohol), separating the diastereomers and converting (e.g., hydrolyzing) the individual diastereomers to the corresponding pure enantiomers. All such isomers, including diastereomer mixtures and pure enantiomers are considered as part of the invention.

The compounds of formula 1 that are basic in nature are capable of forming a wide variety of different salts with various inorganic and organic acids. Although such salts must be pharmaceutically acceptable for administration to animals, it is often desirable in practice to initially isolate the compound of formula 1 from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of the formula 1 that are acidic in nature, are capable of forming base salts with various pharmacologically acceptable cations. Examples of such salts include the alkali metal or alkaline-earth metal salts and particularly, the sodium and potassium salts. These salts may be prepared by conventional techniques. The chemical bases which are used as reagents to prepare the pharmaceutically acceptable base salts of this invention are those which form non-toxic base salts with the acidic compounds of formula 1. Such non-toxic base salts include those derived from such pharmacologically acceptable cations as sodium, potassium calcium and magnesium, etc. These salts can be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product The activity of the compounds of the present invention against bacterial and protozoa pathogens is demonstrated by the compound's ability to inhibit growth of defined strains of human (Assay I) or animal (Assays II and II) pathogens.

ASSAY I

Assay I, described below, employs conventional methodology and interpretation criteria and is designed to provide direction for chemical modifications that may lead to compounds that circumvent defined mechanisms of macrolide resistance. In Assay I, a panel of bacterial strains is assembled to include a variety of target pathogenic species, including representatives of macrolide resistance mechanisms that have been characterized. Use of this panel enables the chemical structure/activity relationship to be determined with respect to potency, spectrum of activity, and structural elements or modifications that may be necessary to obviate resistance mechanisms. Bacterial pathogens that comprise the screening panel are shown in the table below. In many cases, both the macrolide-susceptible parent strain and the macrolide-resistant strain derived from it are available to provide a more accurate assessment of the compound's ability to circumvent the resistance mechanism. Strains that contain the gene with the designation of ermA/ermB/ermC are resistant to macrolides, lincosamides, and streptogramin B antibiotics due to modifications (methylation) of 23S rRNA molecules by an Erm methylase, thereby generally prevent the binding of all three structural classes. Two types of macrolide efflux have been described; msrA encodes a component of an efflux system in staphylococci that prevents the entry of macrolides and streptogramins while mefA/E encodes a transmembrane protein that appears to efflux only macrolides. Inactivation of macrolide antibiotics can occur and can be mediated by either a phosphorylation of the 2'-hydroxyl (mph) or by cleavage of the macrocyclic lactone (esterase). The strains may be characterized using conventional polymerase chain reaction (PCR) technology and/or by sequencing the resistance determinant. The use of PCR technology in this application is described in J. Sutcliffe et al., "Detection Of Erythromycin-Resistant Determinants By PCR", Antimicrobial Agents and Chemotherapy, 40(11), 2562–2566 (1996). The antibacterial assay is performed in microtiter trays and interpreted according to *Performance Standards for Antimicrobial Disk Susceptibility Tests—Sixth Edition; Approved Standard*, published by The National Committee for Clinical Laboratory Standards (NCCLS) guidelines; the minimum inhibitory concentration (MIC) is used to compare strains. acr AB or acr AB-like indicates that an intrinsia multidrug efflux pump exists in the strain. Compounds are initially dissolved in dimethylsulfoxide (DMSO) as 40 mg/ml stock solutions.

| Strain Designation | Macrolide Resistance Mechanism(s) |
| --- | --- |
| *Staphylococcus aureus* 1116 | susceptible parent |
| *Staphylococcus aureus* 1117 | ermB |
| *Staphylococcus aureus* 0052 | susceptible parent |
| *Staphylococcus aureus* 1120 | ermC |
| *Staphylococcus aureus* 1032 | msrA, mph, esterase |
| *Staphylococcus hemolyticus* 1006 | msrA, mph |
| *Streptococcus pyogenes* 0203 | susceptible parent |
| *Streptococcus pyogenes* 1079 | ermB |
| *Streptococcus pyogenes* 1062 | susceptible parent |
| *Streptococcus pyogenes* 1061 | ermB |
| *Streptococcus pyogenes* 1064 | mefA |
| *Streptococcus agalactiae* 1024 | susceptible parent |
| *Streptococcus agalactiae* 1023 | ermB |
| *Streptococcus pneumoniae* 1016 | susceptible |
| *Streptococcus pneumoniae* 1046 | ermB |
| *Streptococcus pneumoniae* 1095 | ermB |
| *Streptococcus pneumoniae* 1175 | mefE |
| *Haemophilus influenzae* 0085 | susceptible; acr AB-like |
| *Haemophilus influenzae* 0131 | susceptible; acr AB-like |
| *Moraxella catarrhalis* 0040 | susceptible |
| *Moraxella catarrhalis* 1055 | erythromycin intermediate resistance |
| *Escherichia coli* 0266 | susceptible; acr AB |
| *Haemophilus influenzae* 1100 | susceptible; acr AB-like |

Assay II is utilized to test for activity against *Pasteurella multocida* and Assay III is utilized to test for activity against *Pasteurella haemolytica*.

ASSAY II

This assay is based on the liquid dilution method in microliter format. A single colony of *P. multocida* (strain 59A067) is inoculated into 5 ml of brain heart infusion (BHI) broth. The test compounds are prepared by solubilizing 1 mg of the compound in 125 $\mu$l of dimethylsulfoxide (DMSO). Dilutions of the test compound are prepared using uninoculated BHI broth. The concentrations of the test compound used range from 200 $\mu$g/ml to 0.098 $\mu$g/ml by two-fold serial dilutions. The *P. multocida* inoculated BHI is diluted with uninoculated BHI broth to make a $10^4$ cell suspension per 200 $\mu$l. The BHI cell suspensions are mixed with respective serial dilutions of the test compound, and incubated at 37° C. for 18 hours. The minimum inhibitory concentration (MIC) is equal to the concentration of the compound exhibiting 100% inhibition of growth of *P. multocida* as determined by comparison with an uninoculated control.

Assay III

This assay is based on the agar dilution method using a Steers Replicator. Two to five colonies isolated from an agar plate are inoculated into BHI broth and incubated overnight at 37 ° C. with shaking (200 rpm). The next morning, 300 μl of the fully grown *P. haemolytica* preculture is inoculated into 3 ml of fresh BHI broth and is incubated at 37° C. with shaking (200 rpm). The appropriate amounts of the test compounds are dissolved in ethanol and a series of two-fold serial dilutions are prepared. Two ml of the respective serial dilution is mixed with 18 ml of molten BHI agar and solidified. When the inoculated *P. haemolytica* culture reaches 0.5 McFarland standard density, about 5 μl of the *P. haemolytica* culture is inoculated onto BHI agar plates containing the various concentrations of the test compound using a Steers Replicator and incubated for 18 hours at 37° C. Initial concentrations of the test compound range from 100–200 μg/ml. The MIC is equal to the concentration of the test compound exhibiting 100% inhibition of growth of *P. haemolytica* as determined by comparison with an uninoculated control.

The in vivo activity of the compounds of formula (I) can be determined by conventional animal protection studies well known to those skilled in the art, usually carried out in mice.

Mice are allotted to cages (10 per cage) upon their arrival, and allowed to acclimate for a minimum of 48 hours before being used. Animals are inoculated with 0.5 ml of a $3 \times 10^3$ CFU/ml bacterial suspension (*P. multocida* strain 59A006) intraperitoneally. Each experiment has at least 3 non-medicated control groups including one infected with 0.1X challenge dose and two infected with 1X challenge dose; a 10X challenge data group may also be used. Generally, all mice in a given study can be challenged within 30–90 minutes, especially if a repeating syringe (such as a Cornwall® syringe) is used to administer the challenge. Thirty minutes after challenging has begun, the first compound treatment is given. It may be necessary for a second person to begin compound dosing if all of the animals have not been challenged at the end of 30 minutes. The routes of administration are subcutaneous or oral doses. Subcutaneous doses are administered into the loose skin in the back of the neck whereas oral doses are given by means of a feeding needle. In both cases, a volume of 0.2 ml is used per mouse. Compounds are administered 30 minutes, 4 hours, and 24 hours after challenge. A control compound of known efficacy administered by the same route is included in each test. Animals are observed daily, and the number of survivors in each group is recorded. The *P. multocida* model monitoring continues for 96 hours (four days) post challenge.

The $PD_{50}$ is a calculated dose at which the compound tested protects 50% of a group of mice from mortality due to the bacterial infection which would be lethal in the absence of drug treatment.

The compounds of formula 1 and their pharmaceutically acceptable salts (hereinafter referred to, collectively, as "the active compounds of this invention") may be administered alone or in combination with pharmaceutically acceptable carriers, in either single or multiple doses. Suitable pharmaceutical carriers include inert solid diluents or fillers, sterile aqueous solutions and various organic solvents. The pharmaceutical compositions formed by combining the active compounds of this invention can then be readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipeints such as sodium citrate, calcium carbonate and calcium phosphate may be employed along with various disintegrants such as starch, methylcellulose, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions containing an active compound of this invention or a pharmaceutically acceptable salt thereof in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The sterile aqueous media employed are all readily available by standard techniques known to those skilled in the art.

To implement the methods of this invention, an effective dose of an active compound of this invention is administered to a susceptible or infected animal (including mammals, fish and birds) by parenteral (i.v., i.m. or s.c.), oral, or rectal routes, or locally as a topical application to the skin and/or mucous membranes. The route of administration will depend on the mammal, fish or bird that is being treated. The effective dose will vary with the severity of the disease, and the age, weight and condition of the animal. However, the daily dose will usually range from about 0.25 to about 150 mg/kg body weight of the patient to be treated, preferably from about 0.25 to about 25 mg/kg.

The Examples provided below illustrate specific embodiments of the invention, but the invention is not limited in scope to the Examples specifically exemplified.

EXAMPLE 1

Compound of formula 1: $R^2=R^3=R^7=H$, $R^1$=phenylbutyl

To a solution of 9-deoxo-9-hydroxyimino-11-deoxy-5-O-desosaminyl-11-(3-phenylbutyl) hydrazo-6-O-methyl-3-oxoerythronolide A, 11,12-carbamate (formula 2, $R_1$=H, $R_2$=phenylbutyl) (50 mg, 0.06 mmol) in $CHCl_3$ (1 mL) was added 37% aqueous $CH_2O$ (25 μL) followed by $HCO_2H$ (23 μL). The resulting solution was heated at 65° C. for 2 hours. The reaction was diluted with saturated $NaHCO_3$, and $CH_2Cl_2$ was added. The organic layer was separated, and the aqueous layer was extracted with $CH_2Cl_2$. The combined organic layers were washed with brine, dried over $MgSO_4$, and concentrated in vacuo. The residue was purified by preparative TLC (89% $CH_2Cl_2$-9% MeOH-1% $NH_3.H_2O$) to afford the title compound as a white solid.

¹H NMR (400 MHz, CDCl₃)δ: 7.28–7.08 (5H, m), 5.36 (1H, d, J=14.4 Hz), 4.91 (1H, dd, J=10.8 and 2.4 Hz), 4.79 (1H, d, J=14.4 Hz), 4.34 (1H, d, J=8.0Hz), 4.28 (1H, d, J=7.2Hz), 3.96 (1H, s), 3.83 (1H, q, J=6.8 Hz), 3.19 (1H, dd, J=7.6 and 10.0 Hz), 3.03 (1H, dq, J=7.6 and 8.0 Hz), 2.79 (3H, s), 2.62 (1H, q, J=6.8 Hz), 2.60 (2H, t, J=7.2 Hz), 2.47 (1H, dt, J=11.2 and 3.6 Hz), 2.27 (6H, s), 1.52 (3H, s), 1.46 (3H, s), 1.35 (3H, d, J=6.8 Hz), 1.30 (3H, d, J=7.6 Hz), 1.29 (3H, d, J=7.6 Hz), 1.23 (3H, d, J=6.4 Hz), 0.99 (3H, d, J=7.2 Hz), 0.82 (3H, t, J=7.6 Hz), Exact mass calcd. for $C_{42}H_{67}N_4O_{10}$ (M+H): 787.4867; found: 787.4863.

EXAMPLE 2

Compound of formula 1: $R^2=R^3=R^7=H$, $R^1$=3-quinolin-4-yl-propyl

To a solution of 9-deoxo-9-hydroxyimino-11-deoxy-5-O-desosaminyl-11-(3-quinolin-4-yl-propyl)hydrazo-6-O-methyl-3-oxoerythronolide A, 11,12-carbamate (formula 2, $R_1$=H, $R_2$=3-quinolin-4-yl-propyl) (187 mg, 0.23 mmol) in CHCl₃ (11 mL) was added 37% aqueous CH₂O (88 μL) followed by HCO₂H (81 μL). The resulting solution was heated at 65° C. for 2 hour. The reaction was diluted with saturated NaHCO₃, and CH₂Cl₂ was added. The organic layer was separated, and the aqueous layer was extracted with CH₂Cl₂. The combined organic layers were washed with brine, dried over MgSO₄, and concentrated invacuo. The residue was purified by preparative TLC (89% CH₂Cl₂-9% MeOH-1% NH₃.H₂O) to afford the title compound as a white solid (121 mg).

¹H NMR (400 MHz, CDCl₃)δ: 8.76 (1H, d, J=4.4 Hz), 8.10 (1H, d, J=8.4 Hz), 8.07 (1H, d, J=8.8 Hz), 7.66 (br. t, J=7.2 Hz), 7.50 (1H, br. t, J=7.2 Hz), 7.27 (1H, d, J=4.8 Hz), 5.54 (1H, d, J=14.4Hz), 4.78 (1H, d, J=14.8 Hz), 3.84 (1H, q, J=6.8Hz), 2.80 (3H, s), 2.30 (6H, s), 2.53 (3H, s), 1.47 (3H, s), 1.35 (3H, d, J=7.2 Hz), 1.33 (3H, d, J=7.6 Hz), 1.29 (3H, d, J=7.2 Hz), 1.23 (3H, d, J=6.0 Hz), 0.99 (3H, d, J=7.2 Hz), and 0.77 (3H, t, J=7.6 Hz).

¹³C NMR (100 MHz, CDCl₃)δ: 203.58, 169.98, 157.63, 154.66, 150.11, 148.25, 147.95, 130.02, 129.01, 127.53, 126.34, 123.73, 121.05, 85.08, 81.07, 78.87, 77.78, 76.61, 70.27, 69.53, 65.89, 56.67, 51.49, 50.93, 50.65, 47.56, 40.23 (2C), 38.30, 31.07, 28.86, 28.35, 28.23, 28.17, 21.76, 21.17, 20.69, 18.82, 15.42, 14.72,13.47,12.55, and 10.37.

Exact mass calcd. for $C_{42}H_{67}N_4O_{10}$(M+H): 824.4810; found: 824.4796.

EXAMPLE 3

Compound of formula 1: $R^2=R^3=R^7=H$, $R^1$=3-(4-phenyl-imidazol-1-yl)-propyl

To a solution of 9-deoxo-9-hydroxyimino-11-deoxy-5-O-desosaminyl-11-(3-(4-phenyl-imidazol-1-yl)-propyl) hydrazo-6-O-methyl-3-oxoerythronolide A, 11,12-carbamate (formula 2, $R_1$=H, $R_2$=3-(4-phenyl-imidazol-1-yl)-propyl) (15 mg, 0.02 mmol) in CHCl₃ (1 mL) was added 37% aqueous CH₂O (7 μL) followed by HCO₂H (7 μL). The resulting solution was heated at 65°0 C. for 2 hours. The reaction was diluted with saturated NaHCO₃, and CH₂Cl₂ was added. The organic layer was separated, and the aqueous layer was extracted with CH₂Cl₂. The combined organic layers were washed with brine, dried over MgSO₄, and concentrated in vacuo. The residue was purified by preparative TLC (89% CH₂Cl₂-9% MeOH-1% NH₃.H₂O) to afford the title compound as a white solid (13 mg).

¹H NMR (400 MHz, CDCl₃)δ: 7.75–7.15 (7H), 5.51 (1H, d, J=14.8 Hz), 4.86 (1H, dd, J=1.6 and 10.4 Hz), 4.71 (1H, d, J=14.8 Hz), 4.32 (1H, d, J=8.4 Hz), 4.27 (1H, d, J=7.2 Hz), 3.93 (1H, s), 3.83 (1H, q, J=6.8 Hz), 2.76 (3H, s), 2.31 (6H, s), 1.53 (3H, s), 1.45 (3H, s), 1.34 (3H, d, J=6.8 Hz), 1.32 (3H, J=6.8 Hz), 1.28 (3H, d, J=7.6 Hz), 1.23 (3H, d, J=6.0 Hz), 0.98 (3H, d, J=7.2 Hz) and 0.80 (3H, t, J=7.2 Hz).

Exact mass calcd. for $C_{44}H_{67}N_6O_{10}$ (M+H): 839.4914; found: 839.4904.

EXAMPLE 4

Compound of formula 1: $R^2=R^3=R^7=H$, $R^1$=3-(2-methoxyphenyl)-propyl

To a solution of 9-deoxo-9-hydroxyimino-11-deoxy-5-O-desosaminyl-11-(3-(2-methoxyphenyl)-propyl)hydrazo-6-O-methyl-3-oxoerythronolide A, 11,12-carbamate (formula 2, $R_1$=H, $R_2$=3-(2-methoxyphenyl)-propyl (15 mg, 0.02 mmol) in CHCl₃ (1 mL) was added 37% aqueous CH₂O (7 μL) followed by HCO₂H (7 μL). The resulting solution was heated at 65° C. for 2 hours. The reaction was diluted with saturated NaHCO₃, and CH₂Cl₂ was added. The organic layer was separated, and the aqueous layer was extracted with CH₂Cl₂. The combined organic layers were washed with brine, dried over MgSO₄, and concentrated in vacuo. The residue was purified by preparative TLC (89% CH₂Cl₂-9% MeOH-1% NH₃.H₂O) to afford the title compound as a white solid (163 mg).

¹H NMR (400 MHz, CDCl₃)δ: 7.13 (2H), 6.79 (2H), 5.48 (1H, d, J=14.8 Hz), 4.95 (1H, dd, J=2.4 and 10.8 Hz), 4.79 (1H, d, J=14.8 Hz), 4.32 (1H, d, J=7.6 Hz), 4.29 (1H, d, J=7.2 Hz), 3.98 (1H, s), 3.76 (3H, s), 2.78 (3H, s), 2.33 (6H, s), 1.52 (3H, s), 1.45 (3H, s), 1.35 (3H, d, J =6.8 Hz), 1.31 (3H, d, J=6.8 Hz), 1.29 (3H, d, J=7.6 Hz), 1.24 (3H, d, J=6.4 Hz), 0.99 (3H, d, J=6.8 Hz) and 0.83 (3H, t, J=7.6 Hz).

MS: m/z 803 (M+H).

EXAMPLE 5

Compound of formula 1: $R^2=R^3=R^7=H$, $R^1$=3-furan-2-yl-propyl

To a solution of 9-deoxo-9-hydroxyimino-11-deoxy-5-O-desosaminyl-11-(3-furan-2-yl-propyl)hydrazo-6-O-methyl-3-oxoerythronolide A, 11,12-carbamate (formula 2, $R_1$=H, $R_2$=3-furan-2-yl-propyl) (15 mg, 0.02 mmol) in CHCl₃ (1 mL) was added 37% aqueous CH₂O (7 μL) followed by HCO₂H (7 μL). The resulting solution was heated at 65° C. for 2 hours. The reaction was diluted with saturated NaHCO₃, and CH₂Cl₂ was added. The organic layer was separated, and the aqueous layer was extracted with CH₂Cl₂. The combined organic layers were washed with brine, dried over MgSO₄, and concentrated in vacuo. The residue was purified by preparative TLC (89% CH₂Cl₂-9% MeOH-1% NH₃.H₂O) to afford the title compound as a white solid.

¹H NMR (400 MHz, CDCl₃)δ: 7.25 (1H), 6.21 (1H), 5.98 (1H), 5.47 (1H, d, J=14.4 Hz), 4.93 (1H, dd, J=2.0 and 10.4 Hz), 4.77 (1H, d, J=14.4 Hz), 4.32 (1H, d, J=7.6 Hz), 4.27 (1H, d, J=7.2 Hz), 3.96 (1H, s), 3.83 (1H, q, J=6.8 Hz), 3.17 (1H, dd, J=7.2 and 10.0 Hz), 2.77 (3H, s), 2.25 (6H, s), 1.52 (3H, s), 1.46 (3H, s), 1.35 (2H, d, J=6.8 Hz), 1.31 (3H, d, J=6.8 Hz), 1.29 (3H, d, J=6.8 Hz), 1.23 (3H, d, J=6.0 Hz), 0.98 (3H, d, J=6.8 Hz), and 0.85 (3H, t, J=7.2 Hz).

MS: m/z 763 (M+H).

EXAMPLE 6

Compound of formula 1: $R^2=R^3=R^7=H$, $R^2$=3-benzoimidazol-1-yl-propyl

To a solution of 9-deoxo-9-hydroxyimino-11-deoxy-5-O-desosaminyl-11-(3-benzoimidazol-1-yl-propyl)hydrazo-6-

O-methyl-3-oxoerythronolide A, 11,12-carbamate (formula 2, $R_1$=H, $R_2$=3-benzoimidazol-1-yl-propyl (15 mg, 0.02 mmol) in $CHCl_3$ (1 mL) was added 37% aqueous $CH_2O$ (7 μL) followed by $HCO_2H$ (7 μL). The resulting solution was heated at 65° C. for 2 hours. The reaction was diluted with saturated $NaHCO_3$, and $CH_2Cl_2$ was added. The organic layer was separated, and the aqueous layer was extracted with $CH_2Cl_2$. The combined organic layers were washed with brine, dried over $MgSO_4$, and concentrated in vacuo. The residue was purified by preparative TLC (89% $CH_2Cl_2$-9% MeOH-1% $NH_3.H_2O$) to afford the title compound as a white solid.

$^1$H NMR (400 MHz, $CDCl_3$)δ: 7.94 (1H, s), 7.77 (1H), 7.46 (1H), 7.24 (2H), 5.52 (1H, d, J =14.4 Hz), 4.90 (1H, dd, J=1.6 and 10.8 Hz), 4.63 (1H, d, J=14.4 Hz), 4.31 (1H, d, J=8.0 Hz), 4.29 (1H, d, J=7.2 Hz), 3.94 (1H, s), 3.83 (1H, q, J=6.8 Hz), 2.74 (3H, s), 2.41 (6H, s), 1.54 (3H, s), 1.43 (3H, s), 1.33 (6H, d, J=6.8 Hz), 1.28 (3H, d, J=7.6 Hz), 1.24 (3H, d, J=6.0 Hz), 0.98 (3H, d, J=7.2 Hz), and 0.82 (3H, t, J=7.2 Hz).

MS: m/z 813 (M+H).

EXAMPLE 7

Compound of formula 1: $R^2$=$R^3$=$R^7$=H, $R^1$=3-indazol-1-yl-propyl

To a solution of 9-deoxo-9-hydroxyimino-11-deoxy-5-O-desosaminyl-11-(3-indazol-1-yl-propyl)hydrazo-6-O-methyl-3-oxoerythronolide A, 11,12-carbamate (formula 2, $R_1$=H, $R_2$=3-indazol-1-yl-propyl) (19 mg, 0.02 mmol) in $CHCl_3$ (1 mL) was added 37% aqueous $CH_2O$ (9 μL) followed by $HCO_2H$ (8 μL). The resulting solution was heated at 65° C. for 2 hours. The reaction was diluted with saturated $NaHCO_3$, and $CH_2Cl_2$ was added. The organic layer was separated, and the aqueous layer was extracted with $CH_2Cl_2$. The combined organic layers were washed with brine, dried over $MgSO_4$, and concentrated in vacuo. The residue was purified by preparative TLC (89% $CH_2Cl_2$-9% MeOH-1% $NH_3.H_2O$) to afford the title compound as a white solid.

$^1$H NMR (400 MHz, $CDCl_3$)δ:7.97 (1H, s), 7.66 (1H, d, J=7.6 Hz), 7.65 (1H, d, J=8.0 Hz), 7.31 (1H, br. t, J=6.0 Hz), 7.07 (1H, br. t, J=6.0 Hz), 5.44 (1H, d, J=14.4 Hz), 4.92 (1H, dd, J=2.4 and 10.4 Hz), 4.43 (1H, d, J=14.4 Hz), 4.30 (1H, t, J=8.0 Hz), 3.95 (1H, s), 3.81 (1H, q, J=6.8 Hz), 2.71 (3H, s), 2.43 (6H, s), 1.54 (3H, s), 1.39 (3H, s), 1.34 (3H, d, J=6.8 Hz), 1.33 (3H, d, J=m6.8 Hz), 1.27 (3H, d, J=7.6 Hz), 1.24 (3H, d, J=6.0 Hz), 0.97 (3H, d, J=6.8 Hz) and 0.82 (3H, t, J=7.6 Hz). MS: m/z 813 (M+H).

EXAMPLE 8

Compound of formula 1: $R^2$=$R^3$=$R^7$=H, $R^1$=3-(4-hydroxy-phenyl)-propyl

To a solution of 9-deoxo-9-hydroxyimino-11-deoxy-5-O-desosaminyl-11-(3-(4-hydroxy-phenyl)-propyl)hydrazo-6-O-methyl-3-oxoerythronolide A, 11,12-carbamate (formula 2, $R_1$=H, $R_2$=3-(4-hydroxy-phenyl)-indol-propyl) (24 mg, 0.03 mmol) in $CHCl_3$ (1 mL) was added 37% aqueous $CH_2O$ (12 μL) followed by $HCO_2H$ (11 μL). The resulting solution was heated at 65° C. for 2 hours. The reaction was diluted with saturated $NaHCO_3$, and $CH_2Cl_2$ was added. The organic layer was separated, and the aqueous layer was extracted with $CH_2Cl_2$. The combined organic layers were washed with brine, dried over $MgSO_4$, and concentrated in vacuo. The residue was purified by preparative TLC (89% $CH_2Cl_2$-9% MeOH-1% $NH_3.H_2O$) to afford the title compound as a white solid.

$^1$H NMR (400 MHz, $CDCl_3$)δ: 6.96 (2H, d, J=8.4 Hz), 6.68 (2H, d, J=8.4 Hz), 5.47 (1H, d, J=14.8 Hz), 4.95 (1H, dd, J=2.4 and 10.8 Hz), 4.78 (1H, d, J=14.8 Hz), 4.34 (1H, d, J=7.6 Hz), 4.27 (1H, d, J=7.2 Hz), 3.98 (1H, s), 3.84 (1H, q, J=7.2 Hz), 3.18 (1H, dd, J=7.2 and 10.4 Hz), 2.80 (3H, s), 2.26 (6H, s), 1.52 (3H, s), 1.46 (3H, s), 1.35 (3H, d, J=6.4 Hz), 1.31 (3H, d, J=6.4 Hz), 1.30 (3H, d, J=6.4 Hz), 1.23 (3H, d, J=6.0 Hz), 0.99 (3H, d, J=7.2 Hz), and 0.83 (3H, t, J=7.2 Hz).

MS: m/z 789 (M+H).

EXAMPLE 9

Compound of formula 1: $R^2$=$R^3$=$R^7$=H, $R^1$=3-(1H-indol-3-yl)-propyl

To a solution of 9-deoxo-9-hydroxyimino-11-deoxy-5-O-desosaminyl-1-(3-(1H-indol-3-yl)-propyl)hydrazo-6-O-methyl-3-oxoerythronolide A, 11,12-carbamate (formula 2, $R_1$=H, $R_2$=3-(1H-indol-3-yl)-propyl) (15 mg, 0.02 mmol) in $CHCl_3$ (1 mL) was added 37% aqueous $CH_2O$ (8 μL) followed by $HCO_2H$ (7 μL). The resulting solution was heated at 65° C. for 2 hours. The reaction was diluted with saturated $NaHCO_3$, and $CH_2Cl_2$ was added. The organic layer was separated, and the aqueous layer was extracted with $CH_2Cl_2$. The combined organic layers were washed with brine, dried over $MgSO_4$, and concentrated in vacuo. The residue was purified by preparative TLC (89% $CH_2Cl_2$-9% MeOH-1% $NH3.H_2O$) to afford the title compound as a white solid.

$^1$H NMR (400 MHz, $CDCl_3$)δ: 7.54 (1H, d, J=7.6 Hz), 7.44 (1H, d, J=8.0 Hz), 7.17 (1H, t, J=7.2 Hz), 7.09 (1H, t, J=6.8 Hz), 6.99 (1H, s), 5.57 (1H, br.s), 5.43 (1H, d, J=14.8 Hz), 4.86 (1H, dd, J=2.4 and 10.8 Hz), 4.76 (1H, d, J=14.8 Hz), 4.23 (1H, d, J=7.2 Hz), 4.22 (1H, d, J=8.4Hz), 3.89 (1H, s), 3.79 (1H, q, J=6.8Hz), 3.16 (1H, dd, J=7.2 and 10.4Hz), 2.44 (3H, s), 2.25 (6H, s), 1.50 (3H, s), 1.36 (3H, d, J=7.2 Hz), 1.29 (3H, d, J=6.8 Hz), 1.26 (3H, d, J=8.0 Hz), 1.21 (3H, d, J=6.0 Hz), 0.96 (3H, d, J=7.2 Hz) and 0.81 (3H, t, J=7.2 Hz).

MS: m/z 812 (M+H).

EXAMPLE 10

Compound of formula 1: $R^2$=$R^3$=$R^7$=H, $R^1$=3-(4-pyridin-3-yl-imidazol-1-yl)-propyl To a solution of 9-deoxo-9-hydroxyimino-11-deoxy-5-O-desosaminyl-11-(3-(4-pyridin-3-yl-imidazol-1-yl)-propyl)hydrazo-6-O-methyl-3-oxoerythronolide A, 11,12-carbamate (formula 2, $R^7$=H, $R^1$=3-(4-pyridin-3-yl-imidazol-1-yl)propyl) (231 mg, 0.28 mmol) in $CHCl_3$ (4 mL) was added 37% aqueous $CH_2O$ (110 μL) followed by $HCO_2H$ (100 μL). The resulting solution was heated at 65° C. for 2 hours. The reaction was diluted with saturated $NaHCO_3$, and $CH_2Cl_2$ was added. The organic layer was separated, and the aqueous layer was extracted with $CH_2Cl_2$. The combined organic layers were washed with brine, dried over $MgSO_4$, and concentrated in vacuo. The residue was purified by preparative TLC (89% $CH_2Cl_2$-9% MEOH-1% $NH_3.H_2O$) to afford the title compound as a white solid.

$^1$H NMR (400 MHz, $CDCl_3$)δ:8.93 (1H, d, J=2.0 Hz), 8.43 (1H, dd, J=1.2,.4 Hz), 8.04 (1H, dt, J=1.6, 7.6 Hz), 7.56 (1H, s), 7.31 (1H, s), 7.24 (1H, dd, J=4.0, 6.4 Hz), 5.52 (1H, d, J=14.4 Hz), 4.85 (1H, d, J=10.8 Hz), 4.71 (1H, d, J=14.8 Hz), 4.32 (1H, d, J=7.6 Hz), 4.21 (1H, t, J=6.8 Hz), 4.01 (1H, m), 3.93 (1H, s), 383 (1H, q, J=6.8 Hz), 2.75 (3H, s), 2.58 (6H, s), 1.33 (6H, d, J=7.2 Hz), 1.27 (3H, d, J=6.0 Hz), 1.25 (3H, d, J=6.2 Hz), 1.00 (3H, d, J=7.2 Hz), and 0.81 (3H, d, J=7.2 Hz).

MS: m/z 840 (M+H).
What is claimed is:
1. A compound of the formula

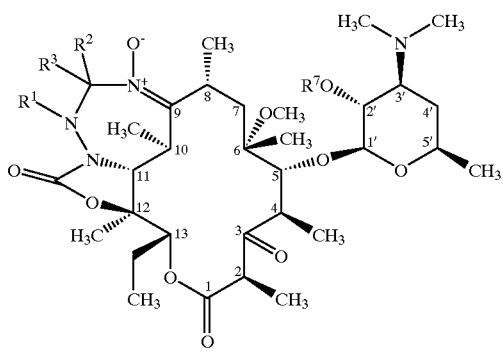

on pharmaceutically acceptable salts thereof, wherein:
$R^1$ is selected from H the group consisting of $-(CR^4R^5)_m R^6$, $-C(O)(CR^4R^5)_m R^6$, $-C(O)O(CR^4R^6)_m R^6$, and $-C(O)NR^4(CR4R^5)_m R^6$, wherein m is an integer ranging from 0 to 6 and both $R^4$ and $R^5$ may vary for each iteration where m is greater than 1;

each $R^2$ and $R^3$ are independently selected from the group consisting of H and $C_1$–$C_{18}$ alkyl, wherein one or two carbons of said alkyl are optionally replaced by a heteroatom selected from the group consisting of O, S and N, and are optionally substituted by 1 to 3 substituents independently selected from the group consisting of $-C(O)O(C_1$–$C_{10})$alkyl, $-O(C_1$–$C_{10})$alkyl, $C_1$–$C_{10}$ alkanoyl, halo, nitro, cyano, $C_1$–$C_{10}$ alkyl, 4–10 membered heterocyclic, $C_6$–$C_{10}$ aryl, $-NH(C_1$–$C_{10})$alkyl, $-S(C_1$–$C_{10}$ alkyl), $-SO(C_1$–$C_{10})$alkyl, $-SO_2(C_1$–$C_{10})$alkyl and $-SO_2N(C_1$–$C_{10})$alkyl, provided that two O atoms, two S atoms or an S and an O atom are not bonded to each other;

each $R^4$ and $R^5$ are independently selected from the group consisting of H, halo and $C_1$–$C_6$ alkyl, wherein 1 to 3 carbons of said alkyl are optionally replaced by a heteroatom selected from the group consisting of O, S and N and each $R^4$ and $R^5$ may vary independently when m is greater than 1, provided that two O atoms, two S atoms or an S and an O atom are not bonded to each other; or each $R^4$ and $R^5$ taken together with the carbon to which they are attached can form a 3–10 membered ring, wherein one or more carbons of said ring are optionally replaced by a heteroatom selected from the group consisting of O, S and N, and are optionally substituted by 1 to 3 substituents independently selected from the group consisting of $-C(O)O(C_1$–$C_{10})$alkyl, $-O(C_1$–$C_{10})$alkyl, $C_1$–$C_{10}$ alkanoyl, halo, nitro, cyano, $C_1$–$C_{10}$ alkyl, 4–10 membered heterocyclic, $C_6$–$C_{10}$ aryl, $-NH(C_1$–$C_{10})$alkyl, $-N((C_1$–$C_{10})$alkyl)$_2$, $-S(C_1$–$C_{10})$alkyl, $-SO(C_1$–$C_{10})$alkyl, $-SO_2(C_2(C_1$–$C_{10})$alkyl and $-SO_2N(C_1$–$C_{10})$alkyl, provided that two O atoms, two S atoms or an S and an O atom are not bonded to each other;

$R^6$ is $(C_1$–$C_{18})$alkyl, a 4–10 membered heterocyclic or $C_6$–$C_{10}$ aryl, wherein 1 to 3 carbons of said alkyl are optionally replaced by a heteroatom selected from the group consisting of O, S and N and said heterocycic and aryl groups are optionally substituted by 1 to 3 substituents independently selected from the group consisting of $-C(O)O(C_1$–$C_{10})$alkyl, $-O(C_1$–$C_{10})$alkyl, $C_1$–$C_{10}$ alkanoyl, halo, nitro, cyano, $(C_1$–$C_{10})$alkyl, $-NH(C_1$–$C_{10})$alkyl, $-N((C_1$–$C_{10})$alkyl)$_2$, $-S(C_1$–$C_{10}$ alkyl), $-SO(C_1$–$C_{10})$alkyl, $-SO_2(C_1$–$C_{10})$alkyl and $-SO_2N(C_1$–$C_{10})$alkyl, provided that two O atoms, two S atoms or an S and an O atom are not bonded to each other; and $R^7$ is H, $-C(O)O(C_1$–$C_{18})$alkyl or $-C(O)(C_1$–$C_{18})$alkyl, wherein 1 to 3 carbons of said alkyl are optionally replaced by a heteroatom selected from the group consisting of O, S and N and wherein in the alkyl portion of said alkanoyl one or two carbons optionally may be replaced by a heteroatom selected from O, S and N, provided that two O atoms, two S atoms or an S and an O atom are not bonded to each other.

2. The compound of claim 1 wherein $R_7$ is H.
3. The compound of claim 1 wherein $R^3$ is H.
4. The compound of claim 1 wherein $R^3=R^2=H$.
5. The compound of claim 1 wherein $R^3=R^2=R^7=H$.
6. The compound of claim 1 wherein wherein $R^1$ is $(CH_2)_m R^6$, wherein m is an integer ranging from 0 to 6.
7. The compound of claim 6 wherein $R^6$ is selected from the group consisting of: quinolin4-yl, quinolin-5-yl, quinolin-8-yl, 4-phenyl-1-imidazol-1-yl, 4-pyridin-3-yl-imidazol-1-yl and imidazo(4,5-b)pyridin-3-yl.
8. The compound of claim 6 wherein m is 3.
9. The compound of claim 8 wherein $R^6$ is selected from the group consisting of: quinolin4-yl, quinolin-5-yl, quinolin-8-yl, 4-phenyl-1-imidazol-1-yl, 4-pyridin-3-yl-imidazol-1-yl and imidazo(4,5-b)pyridin-3-yl.
10. The compound of claim 1 selected from the group consisting of:

the compound of formula 1 wherein $R^7$=H, $R^3=R^2$=H, $R^1$=3-quinolin4-yl-propyl;

the compound of formula 1 wherein $R^7$=H, $R^3=R^2$=H, $R^1$=7-methoxy-quinolin4-yl)-propyl;

the compound of formula 1 wherein $R^7$=H, $R^3=R^2$=H, $R^1$=3-benzoimidazol-1-yl-propyl;

the compound of formula 1 wherein $R^7$=H, $R^3=R^2$=H, $R^1$=3-indol-1-yl-propyl;

the compound of formula 1 wherein $R^7$=H, $R^3=R^2$=H, $R^1$=3-indazol-1-yl-propyl;

the compound of formula 1 wherein $R^7$=H, $R^3=R^2$=H, $R^1$=3-carbazol-1-yl-propyl;

the compound of formula 1 wherein $R^7$=H, $R^3=R^2$=H, $R^1$=3-(5-phenyl-1H-pyrrol-2-yl)-propyl;

the compound of formula 1 wherein $R^7$=H, $R^3=R^2$=H, $R^1$=3-(4-phenyl-imidazol-1-yl)-propyl;

the compound of formula 1 wherein $R^7$=H, $R^3=R^2$=H, $R^1$=3-(imidazo(4,5-b)pyridin-3-yl)-propyl;

the compound of formula 1 wherein $R^7$=H, $R^3=R^2$=H, $R^1$=3-(4-pyridin-3-yl-imidazol-1-yl)-propyl;

the compound of formula 1 wherein $R^7$=H, $R^3=R^2$=H, $R^1$=3-(3-(4-chlorophenyl)-(1,2,4)oxadizol-5-yl)-propyl;

the compound of formula 1 wherein $R^7$=H, $R^3=R^2$=H, $R^1$=3-(3-(4-methoxyphenyl)-(1,2,4)oxadizol-5-yl)-propyl;

the compound of formula 1 wherein $R^7$=H, $R^3=R^2$=H, $R^1$=3-(3-(4-pyridin-4-yl)-(1,2,4)oxadizol-5-yl)-propyl;

the compound of formula 1 wherein $R^7$=H, $R^3=R^2$=H, $R^1$=3-benzotriazol-1-yl-propyl;

the compound of formula 1 wherein $R^7$=H, $R^3=R^2$=H, $R^1$=3-benzotriazol-2-yl-propyl;

the compound of formula 1 wherein $R^7$=H, $R^3$=$R^2$=H, $R^1$=3-(1H-indol-3-yl)-propyl;

the compound of formula 1 wherein $R^7$=H, $R^3$=$R^2$=H, $R^1$=3-pyridin4-yl-propyl;

the compound of formula 1 wherein $R^7$=H, $R^3$=$R^2$=H, $R^1$=3-pyridin-3-yl-propyl;

the compound of formula 1 wherein $R^7$=H, $R^3$=$R^2$=H, $R^1$=3-pyridin-2-yl-propyl;

the compound of formula 1 wherein $R^7$=H, $R^3$=$R^2$=H, $R^1$=3-phenylpropyl;

the compound of formula 1 wherein $R^7$=H, $R^3$=$R^2$=H, $R^1$=3-(2-methoxyphenyl)-propyl;

the compound of formula 1 wherein $R^7$=H, $R^3$=$R^2$=H, $R^1$=3-furan-2-yl-propyl;

the compound of formula 1 wherein $R^7$=H, $R^3$=$R^2$=H, $R^1$=3-thiophen-2-yl-propyl;

the compound of formula 1 wherein $R^7$=H, $R^3$=$R^2$=H, $R^1$=3-thiophen-2-yl-propyl;

the compound of formula 1 wherein $R^7$=H, $R^3$=$R^2$=H, $R^1$=3-pyrrol-1-yl- propyl;

the compound of formula 1 wherein $R^7$=H, $R^3$=$R^2$=H, $R^1$=3-(2-pyridin-3-yl-thiazol-4-yl )-propyl;

the compound of formula 1 wherein $R^7$=H, $R^3$=$R^2$=H, $R^1$=3-(2-phenyl-thiazol-5-yl)-propyl;

the compound of formula 1 wherein $R^7$=H, $R^3$=$R^2$=H, $R^1$=3-(2-phenyl-thiazol-5-yl)-propyl;

the compound of formula 1 wherein $R^7$=H, $R^3$=$R^2$=H, $R^1$=3-(4-phenyl-1H-imidazol-2-yl)-propyl; and pharmaceutically acceptable salts of the foregoing compounds.

11. A pharmaceutical composition for the treatment of a bacterial infection or protozoa infection in a mammal, fish, or bird which comprises a therapeutically effective amount of a compound of claim 1, or a pharmaceutically acceptable salt thereof, and a pharmaceutically acceptable carrier.

12. A method of treating a bacterial infection or a protozoa infection in a mammal, fish, or bird which comprises administering to said mammal, fish, or bird a therapeutically effective amount of a compound of claim 1.

13. A method of preparing a compound of the formula

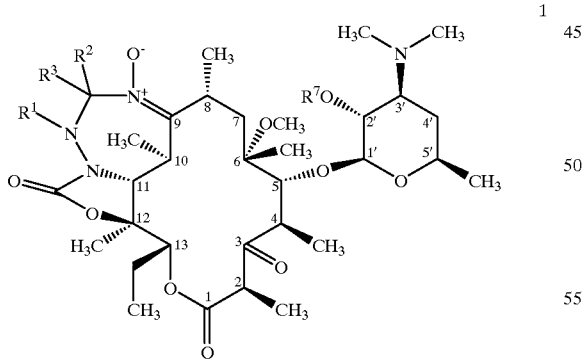

or pharmaceutically acceptable salts thereof, wherein:

$R^1$ is selected from the group consisting of H, —$(CR^4R^5)_m R^6$, —$C(O)(CR^4R^5)_m R^6$, —$C(O)O(CR^4R^5)_m R^6$, and —$C(O)NR^4(CR^4R^5)_m R^6$, wherein m is an integer ranging from 0 to 6 and both $R^4$ and $R^5$ may vary for each iteration where m is greater than 1;

each $R^2$ and $R^3$ are independently selected from the group consisting of H and $C_1$-$C_{18}$ alkyl, wherein one or two carbons of said alkyl are optionally replaced by a heteroatom selected from the group consisting of O, S and N, and are optionally substituted by 1 to 3 substituents independently selected from the group consisting of —$C(O)O(C_1$-$C_{10})$alkyl, —$O(C_1$-$C_{10})$alkyl, $C_1$-$C_{10}$ alkanoyl, halo, nitro, cyano, $C_1$-$C_{10}$ alkyl, 4–10 membered heterocyclic, $C_6$-$C_{10}$ aryl, —NH($C_1$-$C_{10}$)alkyl, —S($C_1$-$C_{10}$ alkyl), —SO($C_1$-$C_{10}$) alkyl, —$SO_2(C_{1-C10})$alkyl and —$SO_2N(C_{1-C10})$alkyl, provided that two O atoms, two S atoms or an S and an O atom are not bonded to each other;

each $R^4$ and $R^5$ are independently selected from the group consisting of H, halo and $C_{1-C6}$ alkyl, wherein 1 to 3 carbons of said alkyl are optionally replaced by a heteroatom selected from the group consisting of O, S and N and each $R^4$ and $R^5$ may vary independently when m is greater than 1, provided that two O atoms, two S atoms or an S and an O atom are not bonded to each other; or each $R^4$ and $R^5$ taken together with the carbon to which they are attached can form a 3–10 membered ring, wherein one or more carbons of said ring are optionally replaced by a heteroatom selected from the group consisting of O, S and N, and are optionally substituted by 1 to 3 substituents independently selected from the group consisting of —$C(O)O(C_1$-$C_{10})$alkyl, —$O(C_1$-$C_{10})$alkyl, $C_1$-$C_{10}$ alkanoyl, halo, nitro, cyano, $C_1$-$C_{10}$ alkyl, 4–10 membered heterocyclic, $C_6$-$C_{10}$ aryl, —NH($C_1$-$C_{10}$)alkyl, —N(($C_1$-$C_{10}$)alkyl)$_2$, —S($C_1$-$C_{10}$)alkyl, —SO ($C_1$-$C_{10}$ )alkyl, —$SO_2(C_2(C_1$-$C_{10})$alkyl and —$SO_2N$ ($C_1$-$C_{10}$)alkyl, provided that two O atoms, two S atoms or an S and an O atom are not bonded to each other;

$R^6$ is ($C_1$-$C_{18}$)alkyl, a 4–10 membered heterocyclic or $C_6$-$C_{10}$ aryl, wherein 1 to 3 carbons of said alkyl are optionally replaced by a heteroatom selected from the group consisting of O, S and N and said heterocycic and aryl groups are optionally substituted by 1 to 3 substituents independently selected from the group consisting of —$C(O)O(C_1$-$C_{10})$alkyl, —$O(C_1$-$C_{10})$ alkyl, $C_1$-$C_{10}$ alkanoyl, halo, nitro, cyano, ($C_1$-$C_{10}$) alkyl, —NH($C_1$-$C_{10}$)alkyl, —N(($C_1$-$C_{10}$)alkyl)$_2$, —S($C_1$-$C_{10}$ alkyl), —SO($C_1$-$C_{10}$)alkyl, —$SO_2$ ($C_1$-$C_{10}$)alkyl and —$SO_2N(C_1$-$C_{10})$alkyl, provided that two O atoms, two S atoms or an S and an O atom are not bonded to each other; and $R^7$ is H, —$C(O)O(C_1$-$C_{18})$alkyl or —$C(O)(C_1$-$C_{18})$alkyl, wherein 1 to 3 carbons of said alkyl are optionally replaced by a heteroatom selected from the group consisting of O, S and N and wherein in the alkyl portion of said alkanoyl one or two carbons optionally may be replaced by a heteroatom selected from the group consisting of O, S and N, provided that two O atoms, two S atoms or an S and an O atom are not bonded to each other, which comprises treating a compound of the formula

2

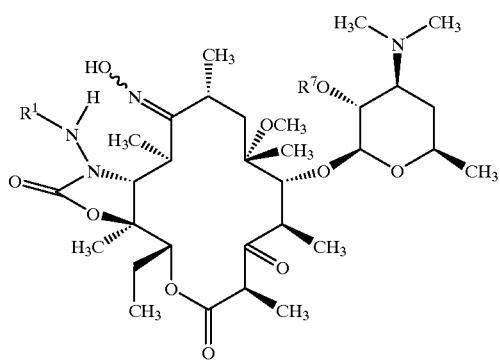

wherein $R^7$ and $R^1$ are as defined above, with a compound of the formula $R^3R^2C=O$, wherein $R^3$ and $R^2$ are as defined for the compound of formula 1, in the presence of an acid.

14. The method of claim 13 wherein the compound of the formula $R^3R^2C=O$ is $CH_2O$.

15. The method of claim 13 wherein the acid is selected from the group consisting of: acetic acid, formic acid, para-toluene sulfonic acid and proprionic acid.

16. A compound of the formula

3

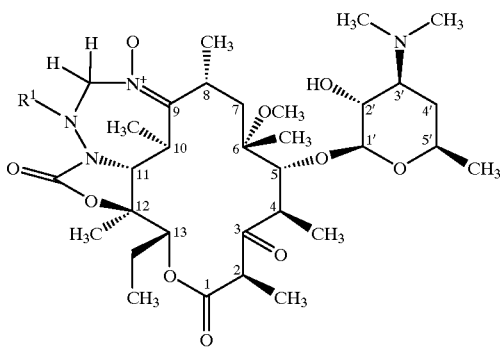

or pharmaceutically acceptable salts thereof, wherein:

$R^1$ is selected from the group consisting of H, —$(CR^4R^5)_m R^6$, —$C(O)(CR^4R^5)_m R^6$, —$C(O)O(CR^4R^5)_m R^6$, and —$C(O)NR^4(CR^4R^5)_m R^6$, wherein m is an integer ranging from 0 to 6 and both $R^4$ and $R^5$ may vary for each iteration where m is greater than 1;

each $R^4$ and $R^5$ are independently selected from the group consisting of H, halo and $C_1$–$C_6$ alkyl, wherein 1 to 3 carbons of said alkyl are optionally replaced by a heteroatom selected from the group consisting of O, S and N and each $R^4$ and $R^5$ may vary independently when m is greater than 1, provided that two O atoms, two S atoms or an S and an O atom are not bonded to each other; or each $R^4$ and $R^5$ taken together with the carbon to which they are attached can form a 3–10 membered ring, wherein one or more carbons of said ring are optionally replaced by a heteroatom selected from the group consisting of O, S and N, and are optionally substituted by 1 to 3 substituents independently selected from the group consisting of —$C(O)O(C_1$–$C_{10})$alkyl, —$O(C_1$–$C_{10})$alkyl, $C_1$–$C_{10}$ alkanoyl, halo, nitro, cyano, $C_1$–$C_{10}$ alkyl, 4–10 membered heterocyclic, $C_{6C10}$ aryl, —$NH(C_1$–$C_{10})$alkyl, —$N((C_1$–$C_{10})$alkyl$)_2$, —$S(C_1$–$C_{10})$alkyl, —$SO(C_1$–$C_{10})$alkyl, —$SO_2(C_2(C_1$–$C_{10})$alkyl and —$SO_2N(C_1$–$C_{10})$alkyl, provided that two O atoms, two S atoms or an S and an O atom are not bonded to each other; and $R^6$ is $(C_1$–$C_{18})$alkyl, a 4–10 membered heterocyclic or $C_6$–$C_{10}$ aryl, wherein 1 to 3 carbons of said alkyl are optionally replaced by a heteroatom selected from the group consisting of O and N and said heterocyic and aryl groups are optionally substituted by 1 to 3 substituents independently selected from the group consisting of —$C(O)O(C_1$–$C_{10})$alkyl, —$O(C_1$–$C_{10})$alkyl, $C_1$–$C_{10}$ alkanoyl, halo, nitro, cyano, $(C_1$–$C_{10})$ alkyl, —$NH(C_1$–$C_{10})$alkyl, —$N((C_1$–$C_{10})$alkyl$)_2$, —$S(C_1$–$C_{10}$ alkyl), —$SO(C_1$–$C_{10})$alkyl, —$SO_2(C_1$–$C_{10})$alkyl and —$SO_2N(C_1$–$C_{10})$alkyl, provided that two O atoms, two S atoms or an S and an O atom are not bonded to each other.

17. A compound of the formula

3

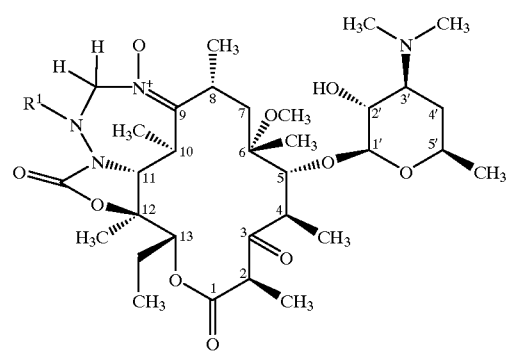

or pharmaceutically acceptable salts thereof, wherein:

$R^1$ is selected from the group consisting of: phenylbutyl, 3-quinolin4-yl-propyl, 3-(4-phenyl-imadazol-1-yl)-propyl, 3-(2-methoxyphenyl)-propyl, 3-furan-2-yl-propyl, 3-benzoimidazol-1-yl-propyl, 3-indazol-1-yl-propyl, 3-(4-hydroxy-phenyl)-propyl, 3-(1H-indol-3-yl)-propyl, and 3-(4-pyridin-3-yl-imidazol-1 -yl)-propyl.

* * * * *